United States Patent
Wong et al.

(10) Patent No.: US 9,044,458 B2
(45) Date of Patent: Jun. 2, 2015

(54) INHIBITION OF TAT ACTIVATING REGULATORY DNA-BINDING PROTEIN 43

(75) Inventors: Philip C. Wong, Lutherville, MD (US); Donald L. Price, Columbia, MD (US); Po-Min Chiang, Tainan (TW)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 13/816,334

(22) PCT Filed: Jul. 26, 2011

(86) PCT No.: PCT/US2011/045372
§ 371 (c)(1),
(2), (4) Date: Apr. 17, 2013

(87) PCT Pub. No.: WO2012/021287
PCT Pub. Date: Feb. 16, 2012

(65) Prior Publication Data
US 2013/0219534 A1    Aug. 22, 2013

Related U.S. Application Data

(60) Provisional application No. 61/371,825, filed on Aug. 9, 2010.

(51) Int. Cl.
| | | |
|---|---|---|
| *A61K 31/713* | (2006.01) | |
| *A61K 39/395* | (2006.01) | |
| *A61K 31/00* | (2006.01) | |
| *A61K 31/7088* | (2006.01) | |
| *C07K 14/47* | (2006.01) | |
| *C12Q 1/68* | (2006.01) | |
| *G01N 33/68* | (2006.01) | |
| *A61K 31/7105* | (2006.01) | |

(52) U.S. Cl.
CPC ............ *A61K 39/3955* (2013.01); *A61K 31/00* (2013.01); *A61K 31/7088* (2013.01); *C07K 14/4702* (2013.01); *C12Q 1/6883* (2013.01); *C12Q 2600/158* (2013.01); *G01N 33/6893* (2013.01); *G01N 2333/4703* (2013.01); *G01N 2800/044* (2013.01); *C12Q 2600/136* (2013.01); *A61K 31/7105* (2013.01); *A61K 31/713* (2013.01)

(58) Field of Classification Search
CPC ........... A61K 2300/00; A61K 39/3955; A61K 31/713; A61K 31/7105; C12Q 1/6883; C12N 15/00; A01K 2227/105; A01K 67/0276; A01K 2217/075; G01N 2800/60; G01N 33/6893
See application file for complete search history.

(56) References Cited

U.S. PATENT DOCUMENTS

| | | |
|---|---|---|
| 7,314,713 B1 | 1/2008 | Shattuck et al. |
| 2005/0255114 A1 | 11/2005 | Labat et al. |
| 2009/0042965 A1 | 2/2009 | Dervan et al. |
| 2009/0104605 A1 | 4/2009 | Siuzdak et al. |
| 2010/0306862 A1* | 12/2010 | Shen et al. ................. 800/3 |

FOREIGN PATENT DOCUMENTS

| | | |
|---|---|---|
| EP | 2192197 A1 | 6/2010 |
| WO | WO-2008122422 A1 | 10/2008 |
| WO | WO-2010042669 A2 | 4/2010 |

OTHER PUBLICATIONS

Caccamo et al. "Rapamycin Rescues TDP-43 Mislocalization and the Associated Low Molecular Mass Neurofilament Instability." The Journal of Biological Chemistry (2009) 284(40): 27416-27424.*
Friedman, J. "Causes and control of excess body fat." Nature (May 2009); 459: pp. 340-342.*
Ahima et al. "Obesity gene therapy: Slimming immature rats." Gene Therapy (2002); 10: pp. 196-197.*
Whitmer et al. "Obesity in middle age and future risk of dementia: a 27 year longitudinal population based study." BMJ 2005;330:(1360): pp. 1-5.*
Ayala et al. "TDP-43 regulates retinoblastoma protein phosphorylation through the repression of cyclin-dependent kinase 6 expression." Proc Natl Acad Sci U S A. Mar. 11, 2008; 105(10): pp. 3785-3789.*
An, D. et al., "TBC1D1 Regulates Insulin- and Contraction-Induced Glucose Transport in Mouse Skeletal Muscle," Diabetes, 59:1358-1365 (2010).
Chiang et al. "Deletion of TDP-43 down-regulates Tbc1d1, a gene linked to obesity, and alters body fat metabolism" Proc Natl Acad Sci USA 107(37):16320-16324 (2010).
Fontanesi, L. et al., "The Porcine *TBC1D1* Gene: Mapping, SNP Idenitifcation, and Association Study with Meat, Carcass and Production Traits in Italian Heavy Pigs," Mol. Biol. Rep., 38:1425-1431 (2011).
Koumanov, F. et al., "Thrifty Tbc1d1 and Tbcld4 Proteins Link Signalling and Membrane Trafficking Pathways," Biochem. J. 403:e9-e11 (2007).
Meyre, D. et al., "R125W Coding Variant in TBC1D1 Confers Risk for Familial Obesity and Contributes to Linkage on Chromosome 4p14 in the French Population," Human Mol. Gen., 17(12):1798-1802 (2008).
Stone, S. et al., "TBC1D1 is a candidate for a Severe Obesity Gene and Evidence for a Gene/Gene Interaction in Obesity Predisposition," Human Mol. Gen., 15(18):2709-2720 (2006).

* cited by examiner

*Primary Examiner* — Thaian N Ton
*Assistant Examiner* — Titilayo Moloye
(74) *Attorney, Agent, or Firm* — Foley Hoag LLP

(57) ABSTRACT

Described herein are methods for detecting, characterizing, preventing, and treating metabolic diseases, including obesity and obesity-associated disorders such as diabetes.

17 Claims, 8 Drawing Sheets

INHIBITION OF TAT ACTIVATING REGULATORY DNA-BINDING PROTEIN 43

RELATED APPLICATIONS

This application is the U.S. National Stage Application of International Application No. PCT/US11/045,372, filed on Jul. 26, 2011, which claims the benefit of U.S. Provisional Application Ser. No. 61/371,825, filed on Aug. 9, 2010; the entire contents of the application is incorporated herein by reference.

GOVERNMENT FUNDING

Work described herein was supported, at least in part, by the National Institutes of Health (NIH) under grants NINDS ROI NS41438. The government may therefore have certain rights to this invention.

BACKGROUND

Metabolic disorders are a collection of health disorders that increase the risk of morbidity and loss of qualify of life. Examples of metabolic disorders include diabetes, obesity, including central obesity (disproportionate fat tissue in and around the abdomen), atherogenic dyslipidemia (these include a family of blood fat disorders, e.g., high triglycerides, low HDL cholesterol, and high LDL cholesterol that can foster plaque buildups in the vascular system, including artery walls), high blood pressure (130/85 mmHg or higher), insulin resistance or glucose intolerance (the inability to properly use insulin or blood sugar), a chronic prothrombotic state (e.g., characterized by high fibrinogen or plasminogen activator inhibitor-1 levels in the blood), and a chronic proinflammatory state (e.g., characterized by higher than normal levels of high-sensitivity C-reactive protein in the blood). Metabolic disorders afflict more than 50 million people in the United States.

Obesity represents the most prevalent of metabolic disorders, afflicting more than 26 percent of U.S. adults. Obesity increases the risk of a wide range of obesity-associated disorders, including high blood pressure, arthritis, elevated cholesterol, coronary artery disease, hypertension, stroke, diabetes, hyperlipidemia and some cancers. (See, e.g., Nishina, P. M. et al. (1994), *Metab.* 43:554-558; Grundy, S. M. & Barnett, J. P. (1990), Dis. Mon. 36:641-731, each of which is expressly incorporated by reference). Obesity is the second leading cause of premature death in the U.S.

There is therefore a great need for new methods for the treatment of metabolic disorders such as obesity and for the identification of novel agents useful in the prevention and treatment of such disorders.

SUMMARY

In some embodiments, the instant invention relates to a method of preventing or treating a metabolic disorders in a subject, including diabetes, obesity and/or obesity-associated disorders. In certain embodiments, the method includes administering to the subject an agent that inhibits TDP-43 expression and/or activity to thereby treat obesity or an obesity-associated disorder. Such agents can include, for example, an anti-TDP-43 antisense nucleic acid molecule, an anti-TDP-43 RNA interference molecule, an anti-TDP-43 antibody, a non-activating form of TDP-43 polypeptide or fragment thereof, a small molecule TDP-43 inhibitor, a ribozyme or zinc finger DNA binding protein. In some embodiments the method also includes the administration of an agent that modulates the expression and/or activity of a gene listed in Table 1.

In some embodiments, the agent modulates a cellular function of the cell selected from the group consisting of: a) expression of a marker listed in Table 1; b) thermogenesis in adipose cells; c) differentiation of adipose cells; d) insulin sensitivity of adipose cells; e) basal respiration or uncoupled respiration; f) insulin secretion of pancreatic beta cells; and g) fat oxidation.

In some embodiments the metabolic disorder is obesity, insulin resistance, hyperinsulinemia, hypoinsulinemia, type II diabetes, hypertension, hyperhepatosteatosis, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, or muscle hypoplasia.

In some embodiments the metabolic disorder is an obesity-associated disorder, such as diabetes; cardiovascular disease; high blood pressure; deep vein thrombosis; osteoarthritis; obstructive sleep apnea; cancer and non-alcoholic fatty liver disease.

In certain embodiments, the instant invention relates to method for increasing fat metabolism in a subject. In some embodiments the method includes the step of administering to the subject an agent that inhibits TDP-43 expression and/or activity to thereby increase fat metabolism. Such agents can include, for example, an anti-TDP-43 antisense nucleic acid molecule, an anti-TDP-43 RNA interference molecule, an anti-TDP-43 antibody, a non-activating form of TDP-43 polypeptide or fragment thereof, a small molecule TDP-43 inhibitor, a ribozyme or zinc finger DNA binding protein. In some embodiments the method also includes the administration of an agent that modulates the expression and/or activity of a gene listed in Table 1. In certain embodiments the subject is obese and/or has diabetes.

In some embodiments, the instant invention relates to a method for increasing fat metabolism by a cell. In some embodiments the method includes contacting the cell (in vivo or in vitro) with an agent that inhibits TDP-43 expression and/or activity to thereby increase the fat metabolism of the cell. Such agents can include, for example, an anti-TDP-43 antisense nucleic acid molecule, an anti-TDP-43 RNA interference molecule, an anti-TDP-43 antibody, a non-activating form of TDP-43 polypeptide or fragment thereof, a small molecule TDP-43 inhibitor, a ribozyme or zinc finger DNA binding protein. In some embodiments the method also includes the administration of an agent that modulates the expression and/or activity of a gene listed in Table 1. In some embodiments the cell is a fibroblast, a myoblast, a myocyte, an adipoblast, an adipocyte, a hepatocyte, or a neural cell.

In some embodiments, the agent modulates a cellular function of the cell selected from the group consisting of: a) expression of a marker listed in Table 1; b) thermogenesis in adipose cells; c) differentiation of adipose cells; d) insulin sensitivity of adipose cells; e) basal respiration or uncoupled respiration; f) insulin secretion of pancreatic beta cells; and g) fat oxidation.

In certain embodiments, the instant invention relates to a method for assessing the efficacy of an agent for increasing fat metabolism in a subject. In some embodiments the method includes the steps of: a) detecting in a first subject sample obtained from the subject at a first point in time the expression and/or activity of TDP-43; b) detecting in a second subject sample obtained at a second point in time the expression and/or activity of TDP-43, wherein the second point in time is subsequent to administration of an agent; and c) comparing the expression and/or activity detected in steps a) and b), wherein a higher expression and/or activity of TDP-43 in the first subject sample than the second subject sample indicates that the agent is effective for increasing fat metabolism in the subject. In some embodiments, between the first point in time and the subsequent point in time, the subject has undergone treatment for a metabolic disorder, has completed treatment for a metabolic disorder, and/or has entered into remission from a metabolic disorder. In some embodiments, the first subject sample and the second subject sample are selected from the group consisting of tissue, whole blood, serum, plasma, buccal scrape, saliva, cerebrospinal fluid, urine, stool, and bone marrow.

In some embodiments, the expression and/or activity of TDP-43 is detected by determining the expression of TDP-43 or a TDP-43 regulated gene listed in Table 1. For example, in some embodiments the expression and/or activity of TDP-43 is detected by determining the level of protein expression TDP-42 or the TDP-43 regulated gene (e.g., by using a reagent that specifically binds with the protein, such as an antibody).

In certain embodiments, the expression and/or activity of TDP-43 is detected by determining the level of a polynucleotide (e.g., mRNA or cDNA) encoding TDP-42 or the TDP-43 regulated gene or a fragment thereof. In some embodiments the method also includes a step of amplifying the polynucleotide.

BRIEF DESCRIPTION OF THE DRAWINGS

FIG. 1A shows targeting at the Tardbp locus and removal of neomycin resistance cassette. Exon 3 is floxed and can be removed upon cre recombinase induction. (P, probe for DNA blotting; E, respective exons; F, Frt sites; L, loxP sites; DTA, diphtheria toxin selection cassette; NeoR, neomycin selection cassette.) FIG. 1B shows DNA blot analysis of the control and targeted ES clones; an Xba I digest produced fragments of, respectively, approximately 22 kbp and approximately 8 kbp from the WT and targeted allele when labeled with the probe P in A. FIG. 1C shows tissue lysates of livers and spinal cords harvested from control, Rosa26-ErCre;Tardbp$^{+/F}$, and Rosa26-ErCre;Tardbp$^{F/F}$ mice treated with tamoxifen for 8 days were subjected to protein blot analyses using antisera against TDP-43 and GAPDH. FIG. 1D shows quantification of TDP-43 level (mean±SEM) in the liver blots shown in C (n=3 independent animals in each group). *P<0.05, P<0.01, *P<0.001.

FIG. 2A shows cumulative body weight changes (in g, mean±SEM) were compared in tamoxifen-treated control, Rosa26-ErCre;Tardbp$^{+/F}$, and Rosa26-ErCre;Tardbp$^{F/F}$ mice (n=5 per group). D0, pretreatment. FIG. 2B shows daily energy intakes (mean±SEM) while on tamoxifen diet, n=5. FIG. 2C shows RER (mean±SEM) was monitored continuously from D0 (pretreatment) to day 7 (1 day before quantitative NMR measurement); n=5.

FIG. 2D shows quantitative NMR measurement (mean±SEM) of body fat in the three mouse groups as in A. Note the selective loss of fat mass in the KO mice, in contrast to lean mass. Black, blue, and red lines indicate control, Rosa26-ErCre;Tardbp$^{+/F}$, and Rosa26-ErCre;Tardbp$^{F/F}$ mice, respectively (n=4 per group, including the two dead mice in the F/F group). FIG. 2E shows mesenteric fatty tissues (arrows) in CAG-ErCre;Tardbp$^{+/+}$, CAG-ErCre;Tardbp$^{+/F}$, and CAG-ErCre;Tardbp$^{F/F}$ mice. FIG. 2F shows H&E staining shows loss of fat content in the white (left column) and brown fat (right column). Immunohistochemical staining using the markers ATGL (second column) and PPAR-γ (third column) to visualize adipocytes found in the subcutaneous white fat. Arrows indicate adipocytes. *P<0.05, P<0.01, *P<0.001. (Scale bar: 100 μm.)

FIG. 3A shows targeting strategies for generation of inducible Tardbp-null (iTDPKO) ES cells. iTDPKOES cells contain one floxed Tardbp allele (floxed TDP) and one disrupted Tardbp allele (iCre), whereas cTDP ES cells contain one WT allele and one disrupted Tardbp allele (iCre). PCR analysis identified an 159-bp (denoted by A) or a 305-bp (denoted by B) fragment corresponding to the WT or floxed allele, respectively. FIGS. 3B and 3C show that 4-HT-treated iTDPKOES cells fail to proliferate and undergo apoptosis. FIG. 3B shows photomicrographs and FIG. 3C shows survival data (three independent pairs, mean±SEM) of the ES cells after 6 and 9 days of treatment with 4-HT. (Scale bar: 300 μm)

FIG. 4A shows protein blot analysis of Tbc1d1 and rfc2 from extracts of iTDPKO ES cells treated with 4-HT. Note the dramatic reduction in levels of TDP-43 whereas PCNA is similar in iTDPKO compared with cTDP ES cells. Antisera against actin used as a loading control. FIG. 4B shows protein blot analysis of Tbc1d1 (Upper) and Tardbp (Middle) in the skeletal muscles of control, CAG-ErCre;Tardbp$^{+/F}$, and CAG-ErCre;Tardbp$^{F/F}$ mice. Note the depletion of TDP-43 and Tbc1d1 in muscle of mice lacking Tardbp. (*P<0.05, P<0.01, *P<0.001)

FIG. 5A shows tissue lysates of livers harvested from 6-wk-old control and Tardbp$^{+/-}$ mice were subjected to protein blot analysis using antisera against TDP-43. The blot was reprobed using an antibody to GAPDH. FIG. 5A shows that comparable levels of TDP-43 were observed in the liver tissues between Tardbp$^{+/-}$ mice and control mice (n=3 pairs of independent animals, mean±SEM). FIG. 5C shows lysates of liver, brain, and spinal cord from control and Tardbp$^{+/-}$ mice subjected to protein blot analysis using an anti-N-terminal TDP-43 antibody. Note that there was no detection of any putative N-terminal fragments of TDP-43 of the predicted molecular weight as a result of deletion of exon 3 in Tardbp$^{+/-}$ mice. An approximate 20 to 25 kDa band observed in liver extract of Tardbp$^{+/-}$ mice is likely nonspecific considering the similar band intensities also seen in that of control. Anti-GAPDH and anti-α-tubulin antisera served as the loading controls for liver and brain/spinal cord, respectively.

FIG. 7A shows relative body weight to day 0 (pretreatment) of control, CAG-ErCre;Tardbp$^{+/F}$, and CAG-ErCre;Tardbp$^{F/F}$ mice induced with tamoxifen diet for 18 days. FIG. 7B shows immunohistochemical staining using the adipocyte-specific markers ATGL (Left) and PPAR-γ (Right) to visualize adipocytes (arrows) found in the interscapular fat. Arrows indicate well formed fat vacuoles in the control and CAG-ErCre;Tardbp$^{+/F}$ mice. Note the positive immunoreactivities of adipocyte markers in the CAG-ErCre;Tardbp$^{F/F}$ mice. (Scale bar: 100 μm.)

FIG. 8A shows the level of TDP-43 and FIG. 8B shows the level of Tbc1d1 in the hindlimb skeletal muscles of induced CAG-ErCre;Tardbp$^{+/F}$ and CAG-ErCre;Tardbp$^{F/F}$ mice compared with control mice. Note the dramatic reduction of TDP-43 and Tbc1d1 in CAG-ErCre;Tardbp$^{F/F}$ mice (n=4), whereas trends toward reduction of TDP-43 and Tbc1d1 were observed in the CAG-ErCre;Tardbp$^{+/F}$ mice (n=4) compared with control mice (n=2), although this decrease was not significant in CAG-ErCre;Tardbp$^{+/F}$ mice by ANOVA with Dunnett post analysis.

BRIEF DESCRIPTION OF THE TABLES

Figure 1:
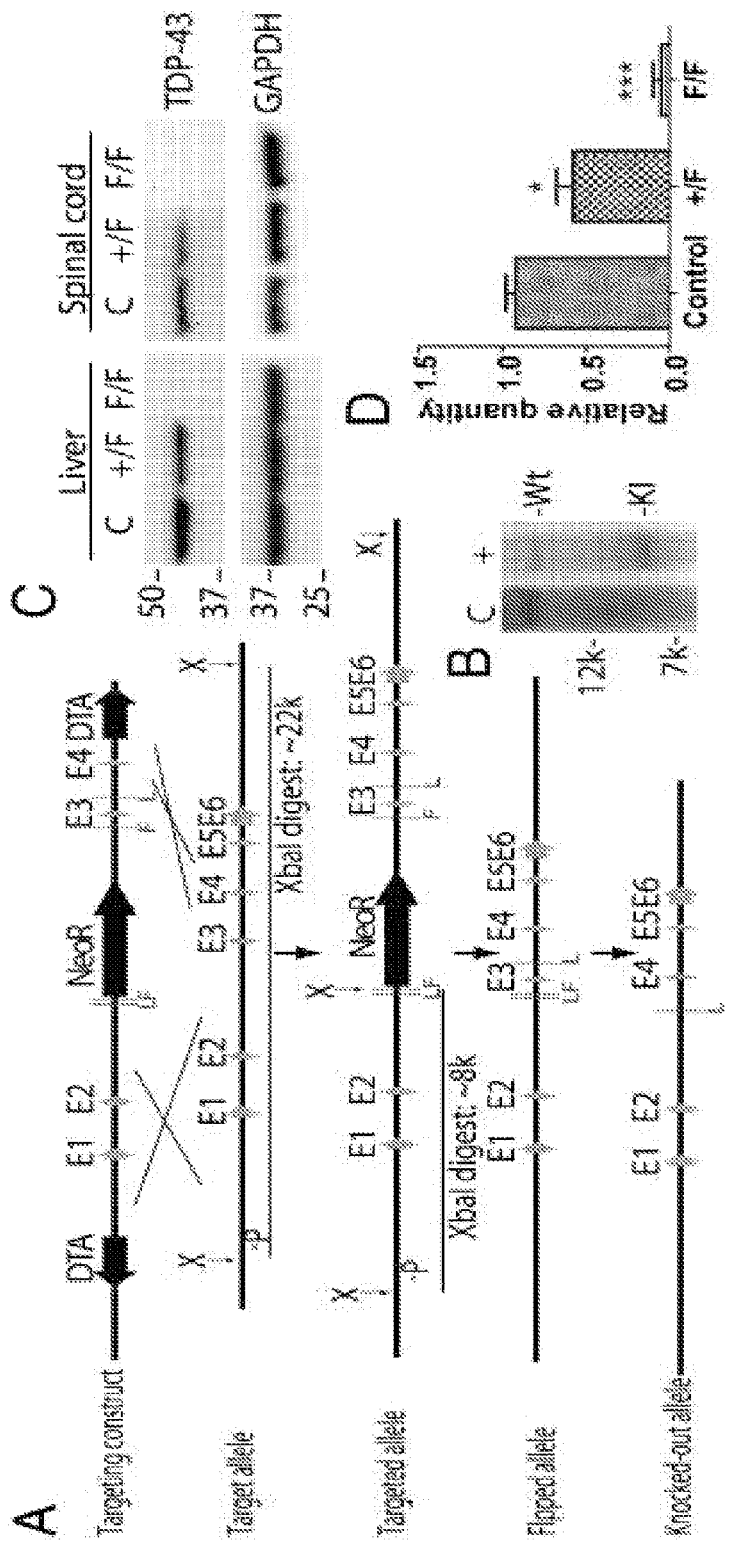
FIGS. 1A-1D shows the strategy and validation for the conditional deletion of Tardbp.

Table 1 shows the top 30 low P value hits of differentially expressed genes identified between control and Tardbp-KO ES cells induced with 100 ng/mL of 4-HT for 3 days.

Table 2 shows summary of RNA-sequencing outputs of iTDPKO and cTDP clones treated with 100 ng/mL 4-HT for 72 hours.

DETAILED DESCRIPTION

Tat Activating Regulator DNA Binding Protein (TDP-43) is a highly conserved metazoan DNA/RNA binding protein involved in RNA transcription and splicing. As described herein, inhibition of TDP-43 results in increased fatty acid metabolism and reduced body fat. Agents that inhibit the activity and/or expression of TDP-43 are useful for the treatment of metabolic disorders, including obesity and diabetes.

I. DEFINITIONS

In order that the present invention may be more readily understood, certain terms are first defined. Additional definitions are set forth throughout the detailed description.

The term "altered level of expression" of a marker, protein or gene (e.g., TDP-43 and the markers set forth in Table 1) refers to an expression level in a test sample (e.g., a sample derived from a subject during or following treatment for a metabolic disorder, such as diabetes and/or obesity), that is greater or less than the standard error of the assay employed to assess expression and may be at least twice, at least two, at least three, at least four, at least five, at least six, at least seven, at least eight, at least nine, or at least ten or more times the expression level in a control sample (e.g., a sample from the subject prior to treatment), or the average expression level of the marker (e.g., markers set forth in Table 1) in several control samples.

The term "altered activity" of a gene, protein and/or marker refers to an activity which is increased or decreased in a test sample (e.g., a sample derived from a subject during or following treatment for a metabolic disorder, such as diabetes and/or obesity), as compared to its activity in a control sample (e.g., a sample from the subject prior to treatment). Altered activity may be the result of, for example, altered expression, altered protein level, altered structure.

Unless otherwise specified here within, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. The term "antibody" as used herein also includes an "antigen-binding portion" of an antibody. The term "antigen-binding portion", as used herein, refers to one or more fragments of an antibody that retain the ability to specifically bind to an antigen Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR).

As used herein, the term "diabetes" refers to a number of well-known conditions. Insulin resistance is defined as a state in which circulating insulin levels in excess of the normal response to a glucose load are required to maintain the euglycemic state (Ford E S, et al. JAMA. (2002) 287:356-9, which is expressly incorporated by reference). Insulin resistance, and the response of a subject with insulin resistance to therapy, may be quantified by assessing the homeostasis model assessment to insulin resistance (HOMA-IR) score, a reliable indicator of insulin resistance (Katsuki A, et al. Diabetes Care 2001; 24:362-5, which is expressly incorporated by reference). The estimate of insulin resistance by the homeostasis assessment model (HOMA)-IR score is calculated with the formula (Galvin P, et al. Diabet Med 1992; 9:921-8): HOMA-IR=[fasting serum insulin (µU/mL)]×[fasting plasma glucose (mmol/L)/22.5]. Subjects with a predisposition for the development of impaired glucose tolerance (IGT) or type 2 diabetes are those having euglycemia with hyperinsulinemia are by definition, insulin resistant. A typical subject with insulin resistance is usually overweight or obese. The term "pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (J. B. Meigs, et al. Diabetes 2003; 52:1475-1484, which is expressly incorporated by reference) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749, which is expressly incorporated by reference). Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or type 2 diabetes. Insulin resistance can be confirmed in these individuals by calculating HOMA-IR score. Insulin resistance may be defined as the clinical condition in which an individual has a HOMA-IR score >4.0 or a HOMA-IR score above the upper limit of normal as defined for the laboratory performing the glucose and insulin assays. Type 2 diabetes is defined as the condition in which a subject has a fasting blood glucose or serum glucose concentration greater than 125 mg/dl (6.94 mmol/L).

A "marker" is a gene, mRNA, or protein which may be altered during the treatment of a disease or disorder (e.g., a metabolic disorder such as diabetes and/or obesity). In some embodiments, the markers described herein include TDP-43 the group of markers listed in Table 1.

The terms "metabolic disorder" include a disorder, disease or condition which is caused or characterized by an abnormal metabolism (i.e., the chemical changes in living cells by which energy is provided for vital processes and activities) in a subject. Metabolic disorders include diseases, disorders, or conditions associated with aberrant thermogenesis or aberrant adipose cell (e.g., brown or white adipose cell) content or function. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response).

Examples of metabolic disorders include obesity, including insulin resistant obesity, diabetes, noninsulin dependent diabetes mellitus (NIDDM or Type II diabetes), insulin dependent diabetes mellitus (IDDM or Type I diabetes), type II diabetes, insulin resistance such as impaired glucose tolerance, glucose intolerance, atherosclerosis, atheromatous disease, heart disease, hypertension, stroke, Syndrome X, hyperphagia, endocrine abnormalities, triglyceride storage disease, Bardet-Biedl syndrome, Lawrence-Moon syndrome, Prader-Labhart-Willi syndrome, Werner's syndrome, dysfunctions associated with lipid biosynthesis, lipid transport, triglyceride levels, plasma levels, and plasma cholesterol, dyslipidemias associated with hyperlipidemia, elevated free fatty acids, hypercholesterolemia, hypertriglyceridemia, elevated low density lipoprotein-(LDL)-cholesterol, elevated very low density lipoprotein-(VLDL)-cholesterol, elevated intermediate density lipoprotein-(IDL)-cholesterol, or reduced high density lipoprotein-(HDL)-cholesterol. A metabolic disorder (e.g., diabetes and/or obesity) is "treated" if at least one symptom of the metabolic disorder (e.g., diabetes and/or obesity) is alleviated, terminated, slowed, or prevented. As used herein, a metabolic disorder (e.g., diabetes and/or obesity) is also "treated" if recurrence or metastasis of the metabolic disorder (e.g., diabetes and/or obesity) is reduced, slowed, delayed, or prevented.

In addition, metabolic disorders are associated with one or more discrete phenotypes. For example, body mass index (BMI) of a subject is defined as the weight in kilograms divided by the square of the height in meters, such that BMI has units of kg/m². In some embodiments, obesity is defined as the condition wherein the individual has a BMI equal to or greater than 30 kg/m². In another aspect, the term obesity is used to mean visceral obesity which can be defined in some embodiments as a waist-to-hip ratio of 1.0 in men and 0.8 in women, which, in another aspect defines the risk for insulin resistance and the development of pre-diabetes. In one embodiment, euglycemia is defined as the condition in which a subject has a fasting blood glucose concentration within the normal range, greater than 70 mg/dl (3.89 mmol/L) and less than 110 mg/dl (6.11 mmol/L). The word fasting has the usual meaning as a medical term. In one embodiment, impaired glucose tolerance (IGT), is defined as the condition in which a subject has a fasting blood glucose concentration or fasting serum glucose concentration greater than 110 mg/dl and less than 126 mg/dl (7.00 mmol/L), or a 2 hour postprandial blood glucose or serum glucose concentration greater than 140 mg/dl (7.78 mmol/L) and less than 200 mg/dl (11.11 mmol/L). The term impaired glucose tolerance is also intended to apply to the condition of impaired fasting glucose. In one embodiment, hyperinsulinemia is defined as the condition in which a subject with insulin resistance, with or without euglycemia, in which the fasting or postprandial serum or plasma insulin concentration is elevated above that of normal, lean individuals without insulin resistance, having a waist-to-hip ration <1.0 (for men) or <0.8 (for women).

In some embodiments, "obesity" refers to a body mass index (BMI) of 30 kg/²m or more (National Institute of Health, Clinical Guidelines on the Identification, Evaluation, and Treatment of Overweight and Obesity in Adults (1998), which is expressly incorporated by reference). However, in some embodiments of the present invention, at least in part, is also intended to include a disease, disorder, or condition that is characterized by a body mass index (BMI) of 25 kg/²m or more, 26 kg/²m or more, 27 kg/²m or more, 28 kg/²m or more, 29 kg/²m or more, 29.5 kg/²m or more, or 29.9 kg/²m or more, all of which are typically referred to as overweight (National Institute of Health, Clinical Guidelines on the Identification, Evaluation, and Treatment of Overweight and Obesity in Adults (1998), which is expressly incorporated by reference). The obesity described herein may be due to any cause, whether genetic or environmental. In one embodiment, "prevention of obesity" refers to preventing obesity or an obesity-associated disorder from occurring if the treatment is administered prior to the onset of the obese condition. Moreover, if treatment is commenced in subjects already suffering from or having symptoms of obesity or an obesity-associated disorder, such treatment is expected to prevent, or to prevent the progression of obesity or the obesity-associated disorder.

The term "obesity-associated disorder" includes all disorders associated with or caused at least in part by obesity. Obesity-associated disorders include, for example, diabetes; cardiovascular disease; high blood pressure; deep vein thrombosis; osteoarthritis; obstructive sleep apnea; cancer and non-alcoholic fatty liver disease.

"Sample," "tissue sample," "subject sample," "subject cell or tissue sample" or "specimen" each refer to a collection of cells obtained from a tissue of a subject or subject. The source of the tissue sample may be solid tissue, as from a fresh, frozen and/or preserved organ, tissue sample, biopsy, or aspirate; blood or any blood constituents, serum, blood; bodily fluids such as cerebral spinal fluid, amniotic fluid, peritoneal fluid or interstitial fluid, urine, saliva, stool, tears; or cells from any time in gestation or development of the subject. The tissue sample may contain compounds that are not naturally intermixed with the tissue in nature such as preservatives, anticoagulants, buffers, fixatives, nutrients, antibiotics or the like.

As used herein, the terms "subject" and "subjects" refer to an animal, e.g., a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee and a human) In some embodiments, the subject or patient is afflicted with a metabolic disorder such as obesity.

As used herein, "Tardbp or TDP-43" refers to Tat activating regulatory DNA-binding protein (Tardbp or TDP-43), a highly conserved metazoan DNA/RNA binding protein thought to be involved in RNA transcription and splicing. (Ou S H, et al. (1995) *J Virol.* 69:3584-3596; Buratti E, et al. (2005) *J Biol Chem.* 280:37572-37584; Buratti E, et al. (2001) *J Biol Chem.* 276:36337-36343; Bose J K, et al. (2008) *J Biol Chem.* 283:28852-28859; Kuo P H, et al. (2009) *Nucleic Acids Res.* 37:1799-1808), each of which is expressly incorporated by reference). TDP-43 has been linked to the pathophysiology of amyotrophic lateral sclerosis and frontotemporal lobar degeneration and is essential for early embryonic development. (Kuo P H, et al. (2009) *Nucleic Acids Res.* 37:1799-1808; Pesiridis G S, et al. (2009) *Hum Mol Genet.* 18(R2):R156-R162; Lagier-Tourenne C, et al. (2009) *Cell.* 136:1001-1004; Neumann M, et al. (2006) *Science.* 314:130-133; Sreedharan J, et al. (2008) *Science.* 319:1668-1672; Kabashi E, et al. (2008) *Nat Genet.* 40:572-574; Wegorzewska I, et al. (2009) *Proc Natl Acad Sci USA.* 106:18809-18814; Li Y, et al. (2010) 107:3169-3174; Wils H, et al. (2010) *Proc Natl Acad Sci USA.* 107:3858-3863; Fiesel F C, et al. (2009) *EMBO J.* 29:209-221; 15. Wu L S, et al. (2009) *Genesis.* 15:15; Sephton C F, et al. (2009) *J Biol Chem.* 285:6826-6834. Kraemer B C, et al. (2010) *Acta Neuropathol.* 119:409-419), each of which is expressly incorporated by reference). For example, representative TDP-43 species, each of which are expressly incorporated by reference, are provided herein as follows:

Mouse TDP-43 nucleotide sequence [Accession: NM_019636.2; GI 120587002] (SEQ ID NO:1).

Mouse TDP-43 amino acid sequence [Accession: Q921F2.1 GI: 20140642] (SEQ ID NO:2).

Human TDP-43 nucleotide sequence [Accession: NM_007375.3 GI: 42741653] (SEQ ID NO:3).

Human TDP-43 amino acid sequence [Accession: Q13148.1 GI: 20140568] (SEQ ID NO:4).

As used herein, "Tbc1d1" refers to a tre-2/USP6, BUB2, cdc16 domain family member 1, a gene associated with human obesity. (Chadt A, et al. (2008) *Nat Genet.* 40:1354-1359; Meyre D, et al. (2008) *Hum Mol Genet.* 17:1798-1802; Stone S, et al. (2006) *Hum Mol Genet.* 15:2709-2720, each of which is expressly incorporated by reference). For example, representative species, each of which are expressly incorporated by reference, are provided herein as follows:

Mouse Tbc1d1 nucleotide sequence [Accession: NM_019636.2 GI: 120587002] (SEQ ID NO:5)

Mouse Tbc1d1 amino acid sequence [Accession: NP_062610.2 GI: 120587003] (SEQ ID NO:6)

Human Tbc1d1 nucleotide sequence [Accession: NM_015173.2 GI: 50658060] (SEQ ID NO:7)

Human Tbc1d1 amino acid sequence [Accession: AAHSO321.3 GI: 54887445] (SEQ ID NO:8)

In certain embodiments, fragments of the sequences listed above (e.g., SEQ ID NOS: 1-8) may be used in the methods described herein. In certain other embodiments, fragments of the genes listed in Table 1 may be used in the methods described herein.

"Treat," "treatment," and other forms of this word refer to the administration of a TDP-43 ligand to impede growth of a metabolic disorder (e.g., diabetes and/or obesity), to cause a metabolic disorder (e.g., diabetes and/or obesity) to be ameliorated, to extend the expected survival time of the subject and/or time to progression of a metabolic disorder or the like.

II. AGENTS THAT INHIBIT EXPRESSION AND/OR ACTIVITY OF TDP-43

Certain embodiments of the present invention relate to methods of increasing fat metabolism, treating metabolic disorders and/or treating obesity or obesity-associated disorders. These methods involve administering an agent that inhibits the activity and/or expression of TDP-43. Agents which may be used to inhibit the activity and/or expression of TDP-43, and to thereby increase fat metabolism, treat metabolic disorders and/or treat obesity or obesity-associated disorders, include antibodies, proteins, peptides, small molecules, RNA interfering agents, e.g., siRNA molecules, shRNA, ribozymes, and antisense oligonucleotides.

Any agent that inhibits TDP-43 can be used to practice certain methods of the invention. Such agents can be those known in the art, or those identified through routine screening assays (e.g. the screening assays described herein).

In some embodiments, assays used to identify agents useful in the methods of the present invention include a the contacting of a cell with a test compound (e.g. the potential agent), to determine the effect of the test compound on the activity and/or expression of TDP-43.

Agents useful in the methods of the present invention may be obtained from any available source, including systematic libraries of natural and/or synthetic compounds. Agents may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85, which is expressly incorporated by reference); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145, which is expressly incorporated by reference).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233, each of which is expressly incorporated by reference.

Libraries of agents may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra., each of which is expressly incorporated by reference).

Agents useful in the methods of the present invention may be identified, for example, using assays for screening candidate or test compounds which inhibit the activity of TDP-43. For example, inhibitors of TDP-43 activity can be identified by contacting a cell with a candidate or test compound and determining the expression of TDP-43 or TDP-43 regulated genes (e.g. the genes listed in Table 1) in the contacted cell.

Inhibitors of TDP-43 expression may also be identified, for example, using methods wherein a cell is contacted with a candidate compound and the expression of TDP-43 mRNA or protein is determined. The level of expression of mRNA or protein in the presence of the candidate compound is compared to the level of expression of mRNA or protein in the absence of the candidate compound. The candidate compound can then be identified as a modulator of TDP-43 expression based on this comparison. For example, when expression of TDP-43 is greater in the presence of the candidate compound than in its absence, the candidate compound is identified as a stimulator of TDP-43 mRNA or protein expression. Conversely, when expression of TDP-43 is less in the presence of the candidate compound than in its absence, the candidate compound is identified as an inhibitor of TDP-43 mRNA or protein expression.

Inhibitors of TDP-43 expression or activity may have one or more of the following biological activities, e.g., 1) modulate the expression of the markers, or fragments thereof, listed in Table 1; 2) increase or stimulate total respiration of a cell; 3) increase fat oxidation in the cell; 4) increase or stimulate uncoupled respiration of a cell; 5) increase or stimulate heat dissipation; 6) modulate thermogenesis; 7) increase or stimulate energy expenditure; and 8) treat metabolic diseases or disorders such as diabetes or obesity.

III. OLIGONUCLEOTIDE INHIBITORS OF TDP-43

In certain embodiments, oligonucleotide inhibitors of TDP-43 are used to increase fat metabolism, treat metabolic disorders and/or treat obesity or obesity-associated disorders. Oligonucleotide inhibitors include, but are not limited to, antisense molecules, siRNA molecules, shRNA molecules, ribozymes and triplex molecules. Such molecules are known in the art and the skilled artisan would be able to create oligonucleotide inhibitors of TDP-43 using routine methods.

Antisense molecules, siRNA or shRNA molecules, ribozymes or triplex molecules may be contacted with a cell or administered to an organism. Alternatively, constructs encoding such molecules may be contacted with or introduced into a cell or organism. Antisense constructs, antisense oligonucleotides, RNA interference constructs or siRNA duplex RNA molecules can be used to interfere with expression of a protein of interest, e.g., TDP-43 protein. Typically at least 15, 17, 19, or 21 nucleotides of the complement of the mRNA sequence are sufficient for an antisense molecule. Typically at least 15, 19, 21, 22, or 23 nucleotides of a target sequence are sufficient for an RNA interference molecule. In some embodiments, an RNA interference molecule will have a 2 nucleotide 3' overhang. If the RNA interference molecule is expressed in a cell from a construct, for example from a hairpin molecule or from an inverted repeat of the TDP-43 gene sequence, then the endogenous cellular machinery may create the overhangs. siRNA molecules can be prepared by chemical synthesis, in vitro transcription, or digestion of long dsRNA by Rnase III or Dicer. These can be introduced into cells by transfection, electroporation, intracellular infection or other methods known in the art. See, for example, each of which is expressly incorporated by reference: Hannon, G J, 2002, RNA Interference, Nature 418: 244-251; Bernstein E et al., 2002, The rest is silence. RNA 7: 1509-1521; Hutvagner G et al., RNAi: Nature abhors a double-strand. Cur. Open. Genetics & Development 12: 225-232; Brummelkamp, 2002, A system for stable expression of short interfering RNAs in mammalian cells. Science 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter S L, and Turner D L. (2002). RNA interference by expression of short-interfering RNAs and hairpin RNAs in mammalian cells. Proc. Natl. Acad. Sci. USA 99(9):6047-6052, PCT publications WO2006/066048 and WO2009/029688, U.S. published application U.S. 2009/0123426, each of which is incorporated by reference in its entirety.

Antisense or RNA interference molecules can be delivered in vitro to cells or in vivo. Typical delivery means known in the art can be used. Any mode of delivery can be used without limitation, including: intravenous, intramuscular, intraperitoneal, intraarterial, local delivery during surgery, endoscopic, subcutaneous, and per os. Vectors can be selected for desirable properties for any particular application. Vectors can be viral, bacterial or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

In the present methods, a RNA interference molecule or an RNA interference encoding oligonucleotide can be administered to the subject, for example, as naked RNA, in combination with a delivery reagent, and/or as a nucleic acid comprising sequences that express the siRNA or shRNA molecules. In some embodiments the nucleic acid comprising sequences that express the siRNA or shRNA molecules are delivered within vectors, e.g. plasmid, viral and bacterial vectors. Any nucleic acid delivery method known in the art can be used in the present invention. Suitable delivery reagents include, but are not limited to, e.g., the Minis Transit TKO lipophilic reagent; lipofectin; lipofectamine; cellfectin; polycations (e.g., polylysine), atelocollagen, nanoplexes and liposomes.

The use of atelocollagen as a delivery vehicle for nucleic acid molecules is described in Minakuchi et al. Nucleic Acids Res., 32(13):e109 (2004); Hanai et al. Ann NY Acad Sci., 1082:9-17 (2006); and Kawata et al. Mol Cancer Ther., 7(9):2904-12 (2008); each of which is incorporated herein in their entirety.

In some embodiments of the invention, liposomes are used to deliver an inhibitory oligonucleotide to a subject. Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In an embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), Proc. Natl. Acad. Sci., USA, 18:6949-53, which is expressly incorporated by reference. In addition, the reduced uptake by the RES lowers the toxicity of stealth liposomes by preventing significant accumulation of the liposomes in the liver and spleen.

IV. ANTIBODY INHIBITORS OF TDP-43

Because of their ability to bind to a particular target with high specificity, antibodies specific for TDP-43 are able to inhibit TDP-43 activity and thereby increase fat metabolism, treat metabolic disorders and/or treat obesity or obesity-associated disorders. Though antibodies most often used to inhibit the activity extracellular proteins (e.g., receptors and/or ligands), the use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology (NY)* 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al., each of which is expressly incorporated by reference). Therefore, antibodies specific for TDP-43 are useful as biological agents for the methods of the present invention.

Antibodies that specifically bind to TDP-43 can be produced using a variety of known techniques, such as the standard somatic cell hybridization technique described by Kohler and Milstein, Nature 256: 495 (1975), which is expressly incorporated by reference. Additionally, other techniques for producing monoclonal antibodies known in the art can also be employed, e.g., viral or oncogenic transformation of B lymphocytes, phage display technique using libraries of human antibody genes.

Polyclonal antibodies can be prepared by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies.

Any of the many well known protocols used for fusing lymphocytes and immortalized cell lines can be applied for the purpose of generating monoclonal antibodies specific against TDP-43 (see, e.g., Galfre, G. et al. (1977) *Nature* 266:55052; Gefter et al. (1977) supra; Lerner (1981) supra; Kenneth (1980) supra), each of which is expressly incorporated by reference. Moreover, the ordinary skilled worker will appreciate that there are many variations of such methods which also would be useful. Typically, an immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. An example of an appropriate mouse cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal antibody specific for TDP-43 can be identified and isolated by screening a recombinant combinatorial immunoglobulin library (e.g., an antibody phage or yeast display library) with the appropriate TDP-43 to thereby isolate immunoglobulin library members that bind TDP-43. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612), and methods for screening phage and yeast display libraries are known in the art. Examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology (NY)* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology (NY)* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554, each of which is expressly incorporated by reference.

In addition, chimeric and humanized antibodies against TDP-43 can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. No. 5,565,332, 5,871,907, or 5,733,743, each of which is expressly incorporated by reference.

In another embodiment, human monoclonal antibodies directed against TDP-43 can be generated using transgenic or transchromosomal mice carrying parts of the human immune system rather than the mouse system. In one embodiment, transgenic mice, referred to herein as "humanized mice," which contain a human immunoglobulin gene miniloci that encodes unrearranged human heavy and light chain variable region immunoglobulin sequences, together with targeted mutations that inactivate or delete the endogenous μ and κ chain loci (Lonberg, N. et al. (1994) *Nature* 368(6474): 856 859, which is expressly incorporated by reference). The mice may also contain human heavy chain constant region immunoglobulin sequences. Accordingly, the mice express little or no mouse IgM or κ, and in response to immunization, the introduced human heavy and light chain variable region transgenes undergo class switching and somatic mutation to generate high affinity human variable region antibodies (Lonberg, N. et al. (1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N. Y Acad. Sci 764:536 546, each of which is expressly incorporated by reference). These mice can be used to generate fully human monoclonal antibodies using the techniques described above or any other technique known in the art. The preparation of humanized mice is described in Taylor, L. et al. (1992) Nucleic Acids Research 20:6287 6295; Chen, J. et al. (1993) International Immunology 5: 647 656; Tuaillon et al. (1993) Proc. Natl. Acad. Sci USA 90:3720 3724; Choi et al. (1993) Nature Genetics 4:117 123; Chen, J. et al. (1993) EMBO J. 12: 821 830; Tuaillon et al. (1994) J. Immunol. 152:2912 2920; Lonberg et al., (1994) Nature 368(6474): 856 859; Lonberg, N. (1994) Handbook of Experimental Pharmacology 113:49 101; Taylor, L. et al. (1994) International Immunology 6: 579 591; Lonberg, N. and Huszar, D. (1995) Intern. Rev. Immunol. Vol. 13: 65 93; Harding, F. and Lonberg, N. (1995) Ann. N.Y. Acad. Sci 764:536 546; Fishwild, D. et al. (1996) Nature Biotechnology 14: 845 851. See further, U.S. Pat. Nos. 5,545,806; 5,569,825; 5,625,126; 5,633,425; 5,789, 650; 5,877,397; 5,661,016; 5,814,318; 5,874,299; and 5,770, 429; all to Lonberg and Kay, and GenPharm International; U.S. Pat. No. 5,545,807 to Surani et al., each of which is expressly incorporated by reference

V. PHARMACEUTICAL COMPOSITIONS

The agents that inhibit the expression and/or activity of TDP-43 can be incorporated into pharmaceutical compositions suitable for administration to a subject. The compositions may contain a single such agent or any combination of modulatory agents described herein and a pharmaceutically acceptable carrier. The pharmaceutical composition may further comprise additional agents useful for increasing fat metabolism or treating metabolic disorders, such as diabetes or obesity.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral, transdermal (topical), transmucosal, and rectal administration.

Toxicity and therapeutic efficacy of the agents described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods described herein of the invention, the therapeutically effective dose can be estimated initially from cell culture assays. A dose can be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Appropriate doses agents depends upon a number of factors within the scope of knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

VI. METHODS OF THE INVENTION

In some embodiments, the present invention relates to a method for increasing fat metabolism, treating a metabolic disorder and/or treating obesity or an obesity-associated disorder by administering to a subject (e.g. a subject in need thereof) an agent that inhibits TDP-43 expression and/or activity.

A subject in need thereof may include, for example, a subject who has been diagnosed with a metabolic disease, a subject who is obese, or a subject who has been treated for a metabolic disease, including subjects that have been refractory to previous treatment. A subject in need thereof may also include, for example, a subject that is predisposed to metabolic diseases, including subjects who are predisposed to obesity, subjects who are overweight and subjects with a family history of metabolic disease.

The term "inhibits TDP-43" is intended to encompass any decrease in expression and/or activity of TDP-43 that promotes, activates, stimulates, or enhances a metabolic response, increases fat metabolism or treats a metabolic disorder, such as obesity or diabetes. In some embodiments, depleted levels of TDP-43 expression or activity results in one or more of the following: 1) modulated the expression of the markers listed in Table 1; 2) increased or stimulated total respiration of a cell; 3) increased fat oxidation; 4) increased or stimulated uncoupled respiration of a cell; 5) increased or stimulated heat dissipation; 6) modulated thermogenesis; 7) increased or stimulated energy expenditure; and 8) treated metabolic diseases or disorders such as diabetes or obesity.

In certain embodiments, the methods described herein encompass the treatment of any metabolic disorder. In certain embodiments, the metabolic disorder treated is obesity, insulin resistance, hyperinsulinemia, hypoinsulinemia, type II diabetes, hypertension, hyperhepatosteatosis, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, or muscle hypoplasia. In certain embodiments the metabolic disorder is an obesity-associated disorder, such as diabetes, cardiovascular disease, high blood pressure, deep vein thrombosis, osteoarthritis, obstructive sleep apnea, cancer or non-alcoholic fatty liver disease In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active agent will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of the subject agent may be determined by reference to the plasma concentrations of the agent. For example, the maximum plasma concentration (Cmax) and the area under the plasma concentration-time curve from time 0 to infinity (AUC (0-4)) may be used. Dosages for the present invention include those that produce the above values for Cmax and AUC (0-4) and other dosages resulting in larger or smaller values for those parameters.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents of the invention employed in the pharmaceutical composition at levels lower than that required in order to achieve the desired therapeutic effect and gradually increase the dosage until the desired effect is achieved.

In general, a suitable daily dose of an agent of the invention will be that amount of the agent which is the lowest dose effective to produce a therapeutic effect. Such an effective dose will generally depend upon the factors described above.

The effectiveness of any particular TDP-43 inhibiting agent to increase fat metabolism or treat metabolic disorders, such as obesity or obesity-associated disorders, can be monitored by comparing the expression or activity of TDP-43 and/or the expression of one or more of the TDP-43 markers listed in Table 1 in two or more samples obtained from a subject undergoing treatment. In general, a first sample is obtained from the subject prior to or concurrant with the beginning of therapy and one or more additional samples are obtained during or after treatment. In such a use, a baseline expression level prior to therapy is determined and then changes from the baseline expression is monitored during the course of therapy. Alternatively, two or more successive samples obtained during treatment can be used without the need of a pre-treatment baseline sample. In such a use, the first sample obtained from the subject is used as a baseline for determining whether marker expression is increasing or decreasing.

Samples obtained from the patient can include tissue samples, whole blood, serum, plasma, buccal scrape, saliva, cerebrospinal fluid, urine, stool, and bone marrow. Other samples can be obtained from different organs, e.g., skin, lung, pancreas, liver, stomach, intestine, heart, reproductive organs, bladder, kidney, urethra and other urinary organs.

Thus, in certain embodiments, the present invention provides a method for assessing the efficacy of an agent that inhibits TDP-43 expression and/or activity for increasing fat oxidation, treating or preventing a metabolic disorder and/or treating or preventing obesity or an obesity-associated disorder, the method including: a) detecting in a first subject sample obtained from the subject at a first point in time the expression and/or activity of TDP-43; b) detecting in a second subject sample obtained at a second point in time the expression and/or activity of TDP-43, wherein the second point in time is subsequent to administration of an agent; and c) comparing the expression and/or activity detected in steps a) and b), wherein a higher expression and/or activity of TDP-43 in the first subject sample than the second subject sample indicates that the agent is effective for increasing fat metabolism in the subject.

This invention is further illustrated by the following examples which should not be construed as limiting. The contents of all references, patents and published patent applications cited throughout this application, as well as the Figures, are incorporated herein by reference.

EXAMPLES

Example 1

Materials and Methods used in Examples 2-6

A. Gene Targeting and ES Cell Culture

The Tardbp gene, isolated from a C57BL/6 genomic BAC clone (RP23-331p21; BACPAC), was characterized by a series of restriction enzyme and generated the targeting vector by DNA recombineering. In the Tardbp targeting vector, the long (7 kb) and short (2.5 kb) arms encompassing exons 1 to 4 of the Tardbp gene were inserted into the PGKneoF2L2DTA vector. The linearized Tardbp targeting vector was electroporated into v26.2 C57BL/6j embryonic stem cells (Open Biosystems), and targeted clones were screened by Southern blot analysis using a flanking probe generated by PCR using mouse DNA via primers 5'-ATGT-GTTGGGTTACAGGCGTGCCTA and 5'-TGACAACTG-TATAATGGGAGATGGCACAG. Two independent targeted clones were injected into albino C57BL/6j mouse blastocysts to generate Tardbp chimeric mice.

Figure 3:
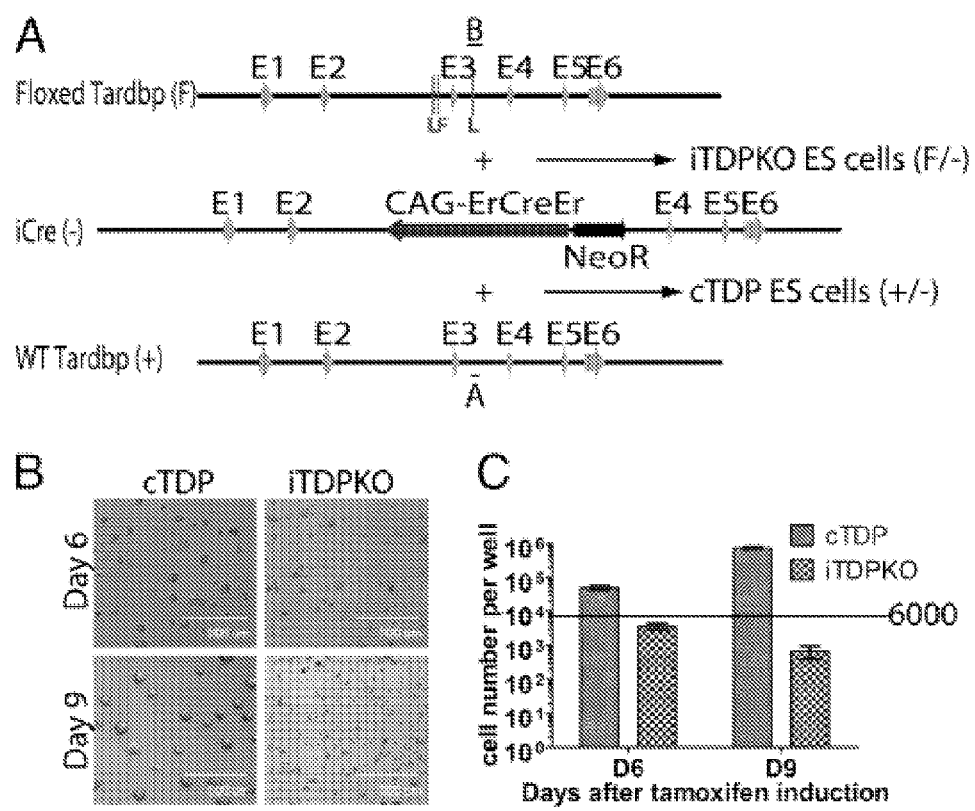
FIGS. 3A-3C show TDP-43 is required for proliferation and survival of ES cells.

The same Tardbp-targeted ES cells used for blastocyst injection were adapted to serum-free culture (2i) conditions (Ying Q L, et al. (2008) *Nature* 453:519-523) for subsequent targeting using a modified pCAG-ERT2CreERT (Addgene 13777) vector (Matsuda T, et al. (2007) *Proc Natl Acad Sci USA* 104:1027-1032; Liu P, et al. (2003) *Genome Res* 13:476-484), with identical homology arms to the Tardbp targeting vector, into the WT or floxed Tardbp allele to generate, respectively, the iTDPKO or cTDP inducible ES cell lines. The correct targeting was validated by PCR analysis using primer sets 5'-AACTTCAAGATCTGACACCCTC-CCC and 5'-GGCCCTGGCTCATCAAGAACTG. The predicted PCR product for WT or floxed alleles is 159 (FIG. 3A) or 305 bp (FIGS. 3A and 3B), respectively. The absence of WT or floxed alleles would represent the identification of iTDPKO or cTDP ES cell clones, respectively. The targeted clones were further validated by protein blot analysis using an antisera specific for TDP-43. Three independent ES cell lines were chosen and established for subsequent analyses.

B. Mouse Breeding

The targeted F1 pups were crossed with a CAG-Cre mouse line (Sakai K, et al (1997) *Biochem Biophys Res Commun* 237:318-324) to generate the standard Tardbp-KO mice lacking exon 3. The same targeted F1 pups were also bred with hACTB-flp mice (Dymecki S M (1996) *Biochem Biophys Res Commun* 237:318-324) to remove the neomycin resistance gene cassette to generate the floxed Tardbp (Tardbp$^{+/F}$) mice. DNA extracted from tail clips of mice were genotyped by PCR using the following sets of primers: 5'-AACTTCAA-GATCTGACACCCTCCCC and 5'-GGCCCTGGCTCAT-CAAGAACTG. The resulting Tardbp$^{+/F}$ mice were then crossed with CAG-ErCre (Jax 004682) (Hayashi S, et al. (2002) *Dev Biol* 244:305-318), or Rosa26-ErCre (Jax 004847) (Badea T C, et al. (2003) *J Neurosci* 23:2314-2322) mice to generate independent lines of tamoxifen-inducible Tardbp-KO mice. For genotyping of germline KO mice, the following set of primers was used: 5'-TCTTACAATGCCTG-GCGTGGTG and 5'-CGTGGTTGCGCACCCTAAC-TATAA. All in vivo experiments were approved by The Johns Hopkins University Animal Care and Use Committee.

C. Metabolic Assessments in Vivo and Body Fat Composition Analysis

ErCre;Tardbp$^{F/F}$ mice, ErCre;Tardbp$^{+/F}$ mice, and controls at 4 to 6 wk of age (n=5 per group) were used for simultaneous assessments of daily body weight change, energy intake (corrected for spillage), and whole-body metabolic profile by indirect calorimetry. Mice without ErCre or with only ErCre (without floxed Tardbp) were used as control. Mice previously maintained on standard rodent chow (no. 2018; Harlan-Teklad) were tested in an open-flow indirect calorimeter (Oxymax Equal Flow; Columbus Instruments). Data were collected for 2 days on baseline diet to confirm acclimation to the calorimetry chambers, and then for the subsequent 8 days on the gene induction diet (no. 2016; Harlan-Teklad), supplemented with tamoxifen (400 mg/kg) and sucrose (5% by weight; diet TD07262; 3.1 kcal/g, 19.7% kcal protein, 70.5% kcal carbohydrate, 9.8% kcal fat). This level of tamoxifen in the diet is consistent with diet-based dosings described previously (Kiermayer C, et al (2007) *Genesis* 45:11-16) and produced similar initial reductions in body weight, necessitating extension of the study for 8 days to acquire more stable, gene-based metabolic data. Rates of oxygen consumption ($VO_2$, mL/kg/h) and $CO_2$ production ($VCO_2$) were measured for each chamber every 16 minutes throughout the study. RER (i.e., $VCO_2/VO_2$) was calculated by Oxymax software (v. 4.02) to estimate relative oxidation of carbohydrate (RER of 1.0) versus fat (RER approaching 0.7), not accounting for protein oxidation. Energy expenditure was calculated as $VO_2 \times [3.815+(1.232 \times RER)]$ (Lusk G (1928) The Elements of the Science of Nutrition (Saunders, Philadelphia), 4th Ed.), and normalized for subject body mass (kcal/kg/h). Average metabolic values were calculated per subject, for each day, and averaged across subjects for statistical analysis. On day 8 of tamoxifen diet feeding, mice were euthanized and carcasses were subjected to quantitative NMR (Echo-MRI 100) at the Phenotyping Core at The Johns Hopkins University to determine lean and fat masses, which were expressed as percent body mass.

D. Histological, Immunohistochemical, and Protein Blot Analysis

The tissue fixation and processing, histological, immunohistochemical staining, biochemical analysis and tissue harvest were performed according to standard protocols previously established in our laboratories. Antibodies used for immunohistochemical or protein blot analysis were anti-Tbc1d1, anti-ATGL, and anti-PPAR-γ (Cell Signaling); anti-GAPDH, anti-α-tubulin, and anti-actin (Sigma-Aldrich); and anti-PCNA (Invitrogen), anti-Tardbp, and anti-RFC2 (Proteintech). Bands were quantified by Quantity One software and normalized by GAPDH or actin level before statistical analysis.

E. RNA-Seq

Independent clones of iTDPKO and cTDP were treated with 100 ng/mL 4-HT for 72 h. Total RNA, harvested from approximately $5 \times 10^6$ cells using a miniRNA kit (Qiagen), was subjected to poly(A)$^+$ RNA selection with oligo-dT magnetic beads (Invitrogen). Procedures recommended by Illumina were used for DNA library construction. Raw reads were mapped to the University of California Santa Cruz mm9 genome library by Efficient Large-Scale Alignment of Nucleotide Databases and the Partek genomic suite was used to generate the set of differentially expressed genes (Table 2).

F. Biological Pathway Analysis

Analysis of the TDP43 KO versus control differentially expressed gene set ($P<e^{-20}$) was performed using the online analysis toolkit WebGestalt (available on the World Wide Web at bioinfo.vanderbilt.edu/webgestalt). WebGestalt was used to search for enriched biological pathways in the open-source Kyoto Encyclopedia of Genes and Genomes database. Using the entire gene set obtained from RNA-seq as a reference set, P values were calculated with the hypergeometric test. Pathways with at least four genes were selected.

G. Statistical Analysis

One-way ANOVA with Dunnett post analysis were used to compare quantity measured among groups. All appropriate numbers indicate measurements from independent animals, and bars on top of each bar indicate SEM. For FIGS. 2A and 2D and FIGS. 7A and 8A and 8B, linear trend post-tests were used to show the dosage effect in the heterozygotes, although the reduction in heterozygotes was not significant in FIGS. 8A and 8B.

Example 2

Tardbp Targeting and Validation

To bypass embryonic lethality of the standard Tardbp-null mice, conditional Tardbp-KO mouse line was generated by engineering a targeting vector in which the third exon of Tardbp was flanked by loxp together with a neomycin resistance gene inserted in the second intron (FIG. 1A); the disrupted Tardbp is predicted to encode a nonfunctional truncated TDP-43 variant as a result of the absence of the critical RNA-binding domain encoded by exon 3 (Kuo P H, et al. (2009) *Nucleic Acids Res* 37:1799-1808) and the highly conserved C-terminal domain. The successful targeting of Tardbp was confirmed by DNA blot analysis (FIG. 1B). The neomycin cassette was subsequently deleted through a cross-breeding strategy with hACTB-flp transgenic mice (Dymecki S M. (1996) *Proc Natl Acad Sci USA*. 93:6191-6196) (floxed Tardbp mice; FIG. 1A). The foxed Tardbp mice were cross-bred with a CAG-Cre transgenic mouse line that express the Cre recombinase ubiquitously (Sakai K, et al. (1997) *Biochem Biophys Res Commun.* 237:318-324) to generate the heterozygous Tardbp-KO (Tardbp$^{+/-}$) mice (FIG. 1A). The Tardbp$^{+/-}$ mice were fertile and expressed similar level of TDP-43 in a variety of tissues compared with those of Tardbp$^{+/+}$ mice (FIGS. 5A-5C), suggesting that the level of TDP-43 is tightly controlled and compensated in the Tardbp$^{+/-}$ mice. However, no live-born Tardbp$^{-/-}$ mice were identified from ten intercrosses of Tardbp$^{+/-}$ mice (number of pups obtained: control/Tardbp$^{+/-}$/Tardbp$^{-/-}$, 23/37/0), confirming that Tardbp is essential for embryogenesis (Wu L S, et al. (2009) *Genesis.* 15:15; Sephton C F, et al. (2009) *J Biol Chem.* 285:6826-6834; Kraemer B C, et al. (2010) *Acta Neuropathol.* 119:409-419).

Figure 5:
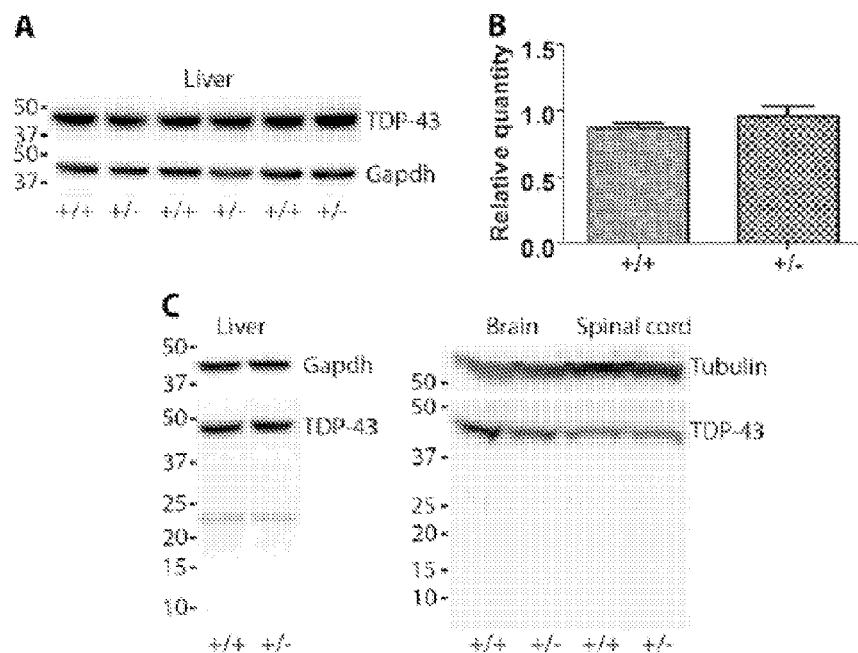
FIGS. 5A-5C show levels of TDP-43 in Tardbp$^{+/-}$ mice.

To examine the physiological role of TDP-43 in postnatal mice, floxed Tardbp mice were bred with Rosa26-ErCre mice to generate inducible Tardbp-KO (ErCre;Tardbp$^{F/F}$) mice in which the Rosa26 enhancer/promoter will direct the expression of ErCre recombinase ubiquitously when it gains access into cell nuclei in the presence of the inducer, tamoxifen. Before tamoxifen induction, the ErCre;Tardbp$^{F/F}$ mice were indistinguishable from ErCre;Tardbp$^{+/F}$ or control littermates. First, it was confirmed that a high percentage of recombination occurred in tamoxifen-treated ErCre;Tardbp$^{F/F}$ mice as determined by the dramatic decrease in levels of TDP-43 protein in tissues from the mice lacking Tardbp (FIG. 1C). In contrast to the Tardbp$^{+/-}$ mice, the conditional Tardbp$^{+/F}$ mice showed a modest reduction in the levels of TDP-43 (FIGS. 1C and 1D). In addition, there was no detection of any N-terminal fragment of TDP-43 that could be generated as a result of the design of the targeting strategy in the brain, spinal cord, or liver of the Tardbp$^{+/-}$ mice (FIG. 5C).

Figure 2:
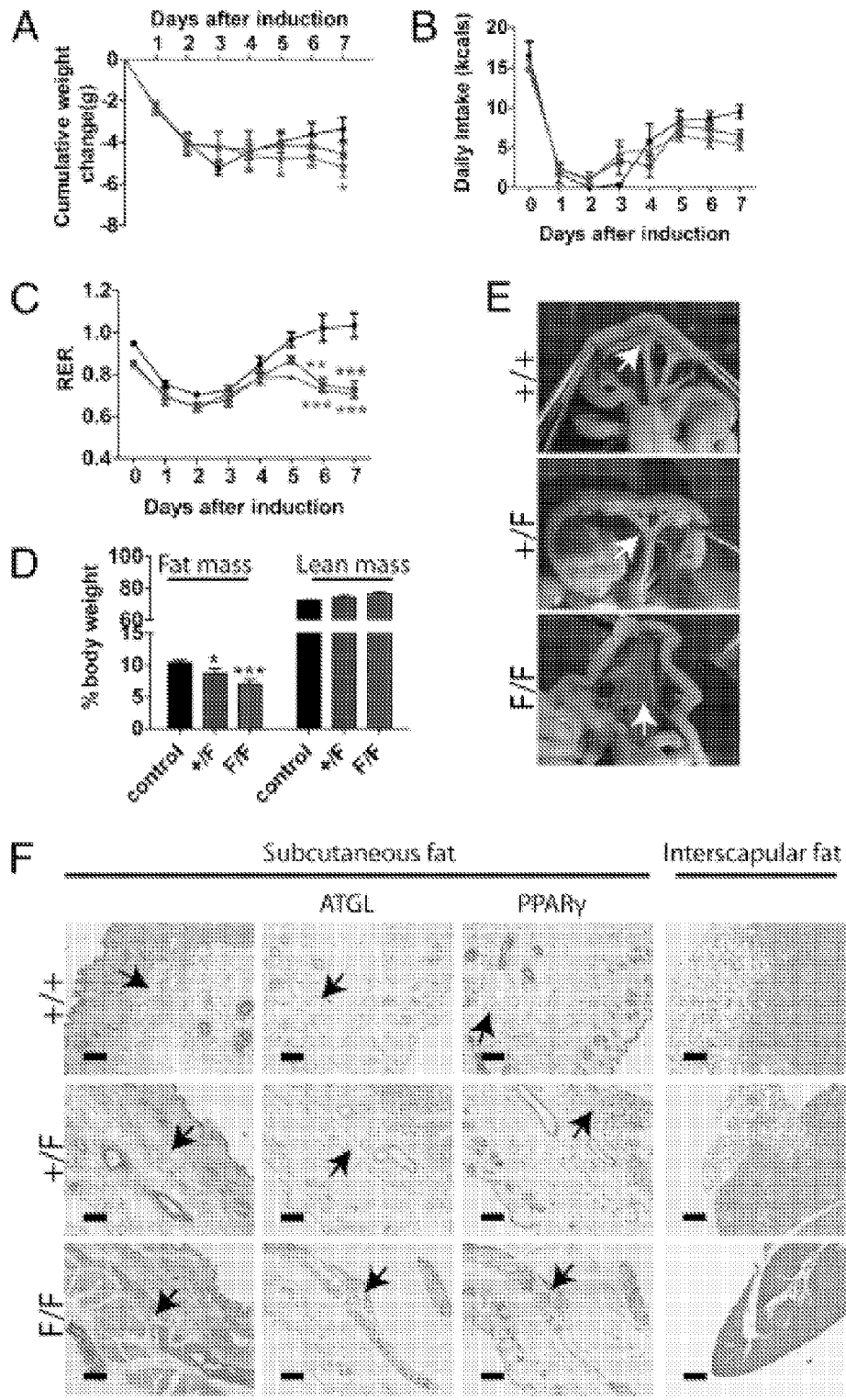
FIGS. 2A-2F shows the phenotype of Tardbp conditional KO mice.
Figure 7:
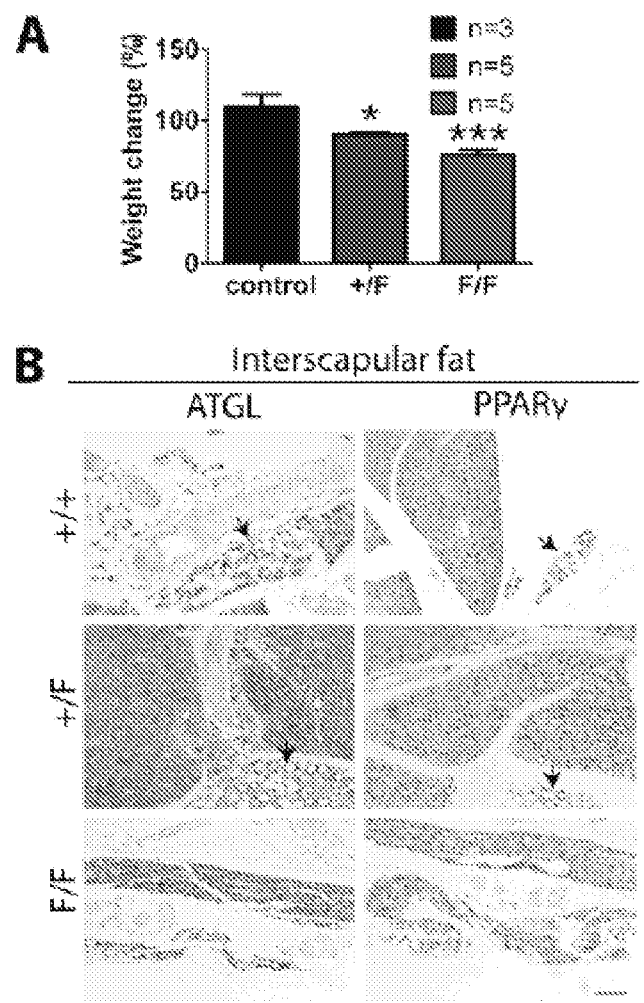
FIGS. 7A-7B show body weights and immunocytochemical analysis of adipocytes of the CAG-ErCre;Tardbp$^{+/F}$ and CAG-ErCre;Tardbp$^{F/F}$ mice.

As the Rosa26-ErCre;TDP$^{F/F}$ mice usually die by day 9 after switching to a tamoxifen-containing diet, a weaker driver line of CAG-ErCre mice (Hayashi S, et al. (2002) *Dev Biol.* 244:305-318.) was used to confirm the observed lean phenotype and to extend the survival time of tamoxifen treated ErCre;Tardbp$^{F/F}$ mice. Most of the CAG-ErCre;Tardbp$^{F/F}$ or CAG-ErCre;Tardbp$^{+/F}$ mice survived at least 18 days after switching to the tamoxifen diet. Moreover, the reduction in levels of TDP-43 in these conditional Tardbp-KO mice correlated with the decrease in body weights (relative body weights on day 18 after treatment with tamoxifen, slope, −0.1687; P<0.001 by linear trend post-test; FIG. 7A). Importantly, gross examination of mesenteric fat confirmed this dramatic fat loss in CAG-ErCre;Tardbp$^{F/F}$ mice (FIG. 2E). Indeed, histological analysis of fatty tissues revealed the absence or reduction, respectively, of fatty vacuoles in adipocytes within subcutaneous tissue (FIG. 2F, first column) and interscapular brown fat (FIG. 2F, fourth column) in the CAG-ErCre;Tardbp$^{F/F}$ or CAG-ErCre;Tardbp$^{+/F}$ mice. Moreover, the positive immunoreactivities of two independent adipocyte markers, adipose triglyceride lipase (ATGL) and peroxisome proliferator-activated receptor-γ (PPAR-γ), showed presence of adipocytes in both white (FIG. 2F, second and third columns) and brown adipose tissues (FIG. 7B), indicating that the loss of fat content is not a result of the absence of adipocytes in these CAG-ErCre;Tardbp$^{F/F}$ mice, but rather caused by a lack of stored fat within the adipocytes. Taken together, the results indicate that the decreased level of TDP-43 is responsible for accelerated fat loss in adipocytes of conditional Tardbp-KO mice through increased fat oxidation.

Example 3

Figure 6:
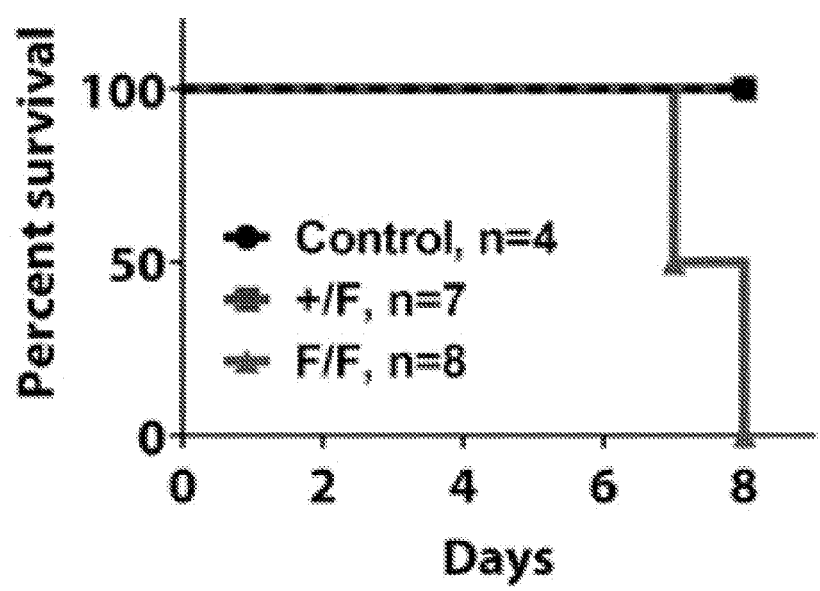
FIG. 6 shows rapid lethality in R26-ErCre;Tardbp$^{F/F}$ mice. Kaplan-Meier survival plot of control, R26-ErCre;Tardbp$^{+/F}$, and R26-ErCre;Tardbp$^{F/F}$ mice following treatment with tamoxifen diet.

Marked Fat Loss and High Fatty Acid Consumption in Conditional Tardbp-KO Mice In contrast to control, Rosa26-ErCre;Tardbp$^{F/F}$ mice unexpectedly die by day 9 after switching to a tamoxifen-containing diet (FIG. 6A). Because initial necropsy analysis of conditional Tardbp-KO mice indicated a loss of body fat, metabolic analyses (Lusk G (1928) The Elements of the Science of Nutrition (Saunders, Philadelphia), 4th Ed.) of these mice were performed. Upon deletion of Tardbp by diet containing tamoxifen citrate (400 mg/kg diet), body weights of all mice decreased during the first 3 days (FIG. 2A) as a consequence of reduced food intake (FIG. 2B). Whereas control mice regained some of their weights during the next 4 days, correlating with increase in food intake, the ErCre; Tardbp$^{F/F}$ or ErCre;Tardbp$^{+/F}$ mice did not regain their body weights despite the increase in food consumption over this same period (cumulative weight loss by d 7, control, −3.36±0.55 g, ErCre;Tardbp$^{+/F}$, −4.59±0.55 g, and ErCre; Tardbp$^{F/F}$, −5.21±0.47 g, ANOVA linear post-test slope, −0.920; P<0.05; n=5 for each group; FIGS. 2A and 2B). Despite significant differences in cumulative weight loss between the control and the Tardbp-KO groups, energy intakes during tamoxifen-dependent deletion of Tardbp were similar among groups (cumulative food intake on day 7, control, 10.8±1.40 kcal vs. ErCre;Tardbp$^{F/F}$, 9.41±0.58 kcal; P>0.05; n=5), suggesting that decreased calorie intake was not the major cause of differences in weight loss. Indirect calorimetry was then used to examine in vivo whether altered metabolism contributed to the relatively greater weight loss in the conditional Tardbp-KO mice. Both ErCre;Tardbp$^{+/F}$ and ErCre;Tardbp$^{F/F}$ mice showed respiratory exchange ratios (RER; defined as VCO$_2$ divided by VO$_2$), indicative of pure fat oxidation (day 7, ErCre;Tardbp$^{+/F}$, 0.73±0.04; ErCre;Tardbp$^{F/F}$, 0.71±0.02), versus the RER of control mice, indicating the high level of carbohydrate oxidation expected based on composition of the specialized tamoxifen-containing diet (day 7, control, 1.03±0.06). The significant decrease in RER in the conditional Tardbp-KO mice by day 6 could not be explained by reduced food intake. Although the initial 3 days on tamoxifen diet did decrease energy intake in all groups of mice, energy intake was subsequently normalized. Interestingly, whereas RER was similar (approximately 0.7) on day 1 and day 7, energy intake on day 7 was much higher than on day 1 (FIGS. 2B and 2C, compare day 1 and day 7). Thus, the results indicate that increased fat oxidation rather than reduced energy intake is responsible for the markedly greater weight loss in the conditional Tardbp-KO mice. Consistent with the calorimetry data, quantitative NMR analysis of the carcasses showed significant decreases in whole body fat mass, but not lean mass, in the ErCre;Tardbp$^{F/+}$ and ErCre; Tardbp$^{F/F}$ mice in a dosage-dependent manner (slope, −1.716; P<0.001 by linear trend post-test; n=4 per group; FIG. 2D). The reduction in levels of TDP-43 in ErCre;Tardbp$^{+/F}$ mice (FIG. 1D) exhibiting altered metabolism suggests that during the acute deletion of one Tardbp allele, the level of TDP-43 has not yet fully compensated whereas levels of TDP-43 in postnatal Tardbp$^{+/-}$ mice have already reached WT level (FIGS. 5A-5C).

Example 4

High-Throughput DNA Sequencing Revealed Downstream Targets of Tardbp

Figure 4:
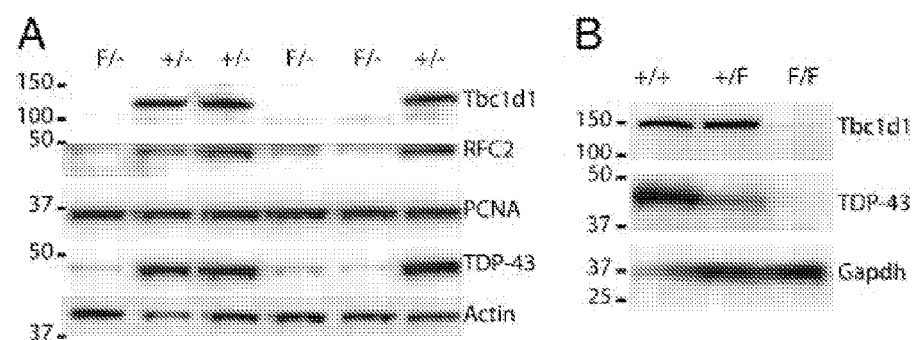
FIGS. 4A-4B show validation of targets identified through deep sequencing analysis.

To identify the downstream targets of TDP-43, the iTDPKO and cTDP ES cells were induced by 100 ng/mL of 4-HT for 3 days and total mRNA were isolated for RNA-seq analysis by Illumina genome analyzer. The raw reads were mapped onto the mm9 mouse genome using the public-domain Efficient Large-Scale Alignment of Nucleotide Databases, and these data were analyzed by the Partek software to identify a set of differentially expressed genes (Table 1). The dramatic reduction in level of Tardbp mRNA (Table 1) validated the deletion of Tardbp in the ES cells and the methodology of RNA-seq analysis. Significantly, protein blot analysis revealed that levels of Rfc2 and Tbc1d1, two of the top hits (Table 1), were nearly abolished in iTDPKO cells (FIG. 4A, upper two panels). Interestingly, among the top 30 hits (i.e., genes with the lowest P values and more than threefold change; Table 1), most (26 of 30) of the genes are down-regulated, suggesting that TDP-43 plays an important role in elevating RNA transcription or maintaining RNA stability.

Example 5

Marked Reduction of Tbc1d1 in Skeletal Muscle of Conditional Tardbp-KO Mice

Figure 8:
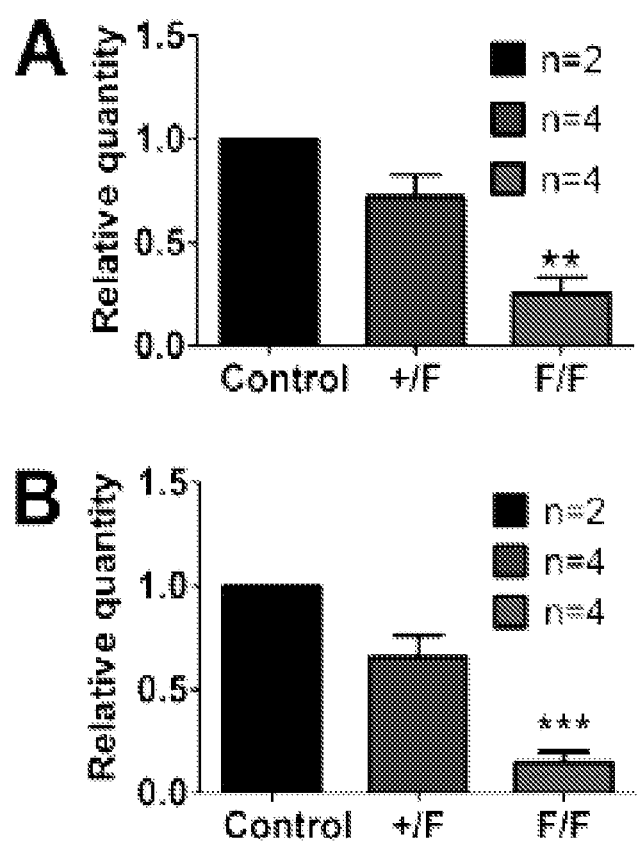
FIGS. 8A-8B show quantification of Tbc1d1 level in the skeletal muscle of Tardbp conditional KO mice.

Tbc1d1, a critical protein associated with human obesity (Meyre D, et al. (2008) Hum Mol Genet. 17:1798-1802., Stone S, et al. (2006) Hum Mol Genet. 15:2709-2720), was drastically reduced in the Tardbp deleted iTDPKO cells (−7.35 fold, P=7.02E-228). As it has been reported that a nonfunctional Tbc1d1 mutant in the skeletal muscle is responsible for the lean phenotype in mice and that Tbc1d1 is essential for Glut4 translocation to the plasma membrane of skeletal muscle cells for glucose uptake (Chadt A, et al. (2008) Nat Genet. 40:1354-1359), a decrease in Tbc1d1 in skeletal muscle might offer an explanation for the lean phenotype shown in the conditional Tardp-KO mouse model (FIGS. 2A-2F). To test this notion, the levels of Tbc1d1 were assessed in the skeletal muscles of the control, CAG-ErCre; Tardbp$^{+/F}$, and CAG-ErCre;Tardbp$^{F/F}$ mice fed with tamoxifen. Protein blot analysis of muscle extracts showed depletion of Tbc1d1 in CAG-ErCre;Tardbp$^{F/F}$ mice (FIG. 4B) that exhibited marked reduction of fat (FIGS. 2E, 2F, 7A, 7B). In addition, correlating with the reduction of TDP-43 protein level (slope=−0.3714; P=0.0015, linear trend post test; FIG. 8A), there is a trend toward reduction of Tbc1d1 in muscles of CAG-ErCre;Tardbp$^{+/F}$ mice, (slope, −0.4256; P=0.0003, linear trend post-test; FIG. 8B), consistent with the mild loss of body weight in the CAG-ErCre;Tardbp$^{+/F}$ mice (FIG. 7A). As the RNA-seq analysis demonstrated that Tardbp deletion is responsible for the marked reduction of Tbc1d1 coupled with the previous report showing the functional requirement of Tbc1d1 in skeletal muscle for the maintenance of fat content in mice (Chadt A, et al. (2008) Nat Genet. 40:1354-1359), the data are consistent with the view that the postnatal deletion of Tardbp led to the lean phenotype through reduction of level of Tbc1d1 protein in the muscle of conditional Tardbp-null mice.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org, the National Center for Biotechnology Information (NCBI) on the world wide web at ncbi.nlm.nih.gov, or miRBase on the world wide web at microrna.sanger.ac.uk.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for reducing body fat mass in a subject, the method comprising administering to the subject an oligonucleotide molecule that inhibits the expression of Tat activating regulatory DNA-binding protein 43 (TDP-43) to thereby reduce body fat mass in the subject.

2. The method of claim 1, wherein the subject further has a decreased respiratory exchange ratio.

3. The method of claim 1, wherein the subject further has increased fat oxidation.

4. The method of claim 1, wherein the subject further has weight loss.

5. The method of claim 1, wherein the body fat mass is whole body fat mass.

6. The method of claim 1, wherein the oligonucleotide is an antisense oligonucleotide that binds to mRNA encoding TDP-43.

7. The method of claim 1, wherein the oligonucleotide is an siRNA specific for TDP-43.

8. The method of claim 1, wherein the oligonucleotide is an shRNA specific for TDP-43.

9. A method for reducing body fat mass in a subject, the method comprising administering to the subject an agent that: (i) binds to Tat activating regulatory DNA-binding protein 43 (TDP-43) and (ii) inhibits the ability of TDP-43 to regulate a TDP-43 regulated gene, to thereby reduce body fat mass in the subject.

10. The method of claim 9, wherein the agent is a small molecule.

11. The method of claim 9, wherein the agent is a nucleic acid.

12. The method of claim 9, wherein the agent is an anti-TDP-43 antibody or a non-activating form of TDP-43 polypeptide or fragment thereof.

13. The method of claim 9, wherein the subject is a human.

14. The method of claim 9, wherein the subject further has a decreased respiratory exchange ratio.

15. The method of claim 9, wherein the subject further has increased fat oxidation.

16. The method of claim 9, wherein the subject further has weight loss.

17. The method of claim 9, wherein the body fat mass is whole body fat mass.

* * * * *